(12) United States Patent
Havard

(10) Patent No.: US 7,406,428 B1
(45) Date of Patent: Jul. 29, 2008

(54) METHOD OF CREATING A VIRTUAL HEALTH CARE NETWORK

(75) Inventor: L. Cade Havard, Dallas, TX (US)

(73) Assignee: Ecom Benefits, Inc., Dallas, TX (US)

( * ) Notice: Subject to any disclaimer, the term of this patent is extended or adjusted under 35 U.S.C. 154(b) by 1121 days.

(21) Appl. No.: 09/753,879

(22) Filed: Jan. 3, 2001

(51) Int. Cl.
*G06Q 40/00* (2006.01)

(52) U.S. Cl. .............................. 705/4; 705/2

(58) Field of Classification Search .................. 705/2–4
See application file for complete search history.

(56) References Cited

U.S. PATENT DOCUMENTS

| | | | | |
|---|---|---|---|---|
| 5,557,514 | A * | 9/1996 | Seare et al. | 705/2 |
| 5,706,441 | A * | 1/1998 | Lockwood | 705/3 |
| 5,845,254 | A * | 12/1998 | Lockwood et al. | 705/2 |
| 6,067,522 | A * | 5/2000 | Warady et al. | 705/2 |
| 6,092,047 | A * | 7/2000 | Hyman et al. | 705/4 |
| 6,223,164 | B1 * | 4/2001 | Seare et al. | 705/2 |
| 6,370,511 | B1 * | 4/2002 | Dang | 705/3 |
| 6,542,905 | B1 * | 4/2003 | Fogel et al. | 707/200 |
| 6,735,569 | B1 * | 5/2004 | Wizig | 705/4 |
| 6,751,630 | B1 * | 6/2004 | Franks et al. | 707/102 |
| 2002/0123905 | A1 * | 9/2002 | Goodroe et al. | 705/2 |
| 2002/0147617 | A1 * | 10/2002 | Schoenbaum et al. | 705/4 |

OTHER PUBLICATIONS

"For Health Benefits, Point and Click", Leonard Bill, Jul. 2000, HRMagazine,45,7,42, Dialog File 149, Acc. No. 01924140.*

"Webster's Ninth New Collegiate Dictionary", A Merriam-Webster INC., Publishers, Springfield, Massachusetts, U.S.A., copyright 1985, p. 736.*

For Health Benefits, Point and Click by Leonard Bill, (HRMagazine 45, 7, 42, Jul. 2000). pp. 1-4.*

For Health Benefits, Point and Click by Bill Leonard; Jul. 200; pp. 1-4.*

For Health Benefits, Point and Click by Leonard Bill, (HR Magazine 45, 7, 42, Jul. 2000).*

For Health Benefits, Point and Click by Leonard Bill (HR Magazine 45, 7, 42, Jul. 2000.*

Alternatives to traditional capitation in managed care agreements, Healthcare Financial Management, Westchester, Apr. 1998 by Kevin M. Kennedy; Daniel J. Merlino.*

* cited by examiner

*Primary Examiner*—Vanel Frenel
(74) *Attorney, Agent, or Firm*—McKee, Voorhees & Sease, P.L.C.

(57) ABSTRACT

The invention includes a new method of creating a client-specific virtual managed care network spanning multiple states. The method seeks to maximize savings while minimizing the inconvenience and disruption to plan participants in changing health care providers. Based on the utilization or disruption data and projected future savings, one or more managed care networks is selected per state. The various managed care networks selected for each state comprise a virtual health care network for providing health care services to health care plan participants. The present invention also includes a new method of predicting future health care savings based upon the selection of a particular managed care network.

6 Claims, 3 Drawing Sheets

METHOD OF CREATING A VIRTUAL HEALTH CARE NETWORK

BACKGROUND OF THE INVENTION

1. Field of the Invention

This present invention relates generally to health care insurance products and services. More particularly, though not exclusively, the present invention relates to a new method of selecting health care plans and a method of creating a virtual health care network.

2. Problems in the Art

Health care in America is changing rapidly. Twenty-five years ago, most people in the United States had indemnity insurance coverage. A person with indemnity insurance could go to any doctor, hospital, or other provider (which would bill for each service given), and the insurance and the patient would each pay part of the bill. But today, it is estimated that more than half of all Americans who have health insurance are enrolled in some kind of managed care plan, an organized way of both providing services and paying for them. Different types of managed care plans include preferred provider organizations (PPOs), health maintenance organizations (HMOs), and point-of-service (POS) plans.

Indemnity and managed care plans differ in their basic approach. Put broadly, the major differences concern choice of providers, out-of-pocket costs for covered services and how bills are paid. Usually, indemnity plans offer more choice of doctors (including specialists, such as cardiologists and surgeons), hospitals and other health care providers than managed care plans. Indemnity plans pay their share of costs of a service only after they receive a bill.

In contrast, managed care plans have agreements with certain doctors, hospitals, and health care providers to give a range of services to plan members/participants at reduced cost. PPOs have become a quite popular form of managed care. A PPO has arrangements with doctors, hospitals and other providers of care who have agreed to accept lower fees from the insurer for their services. As a result, cost sharing is generally lower than if a participant goes outside the network. In addition to the PPO doctors making referrals, plan participants can refer themselves to other doctors, including ones outside of the plan. If the plan participant goes to a doctor within the PPO network, the participant will pay a co-payment (i.e., a set amount for certain services). The coinsurance is based on lower charges for PPO participants. If the plan participant chooses to go outside the network, the participant will have to meet a deductible and pay coinsurance based on higher charges. In addition, the participant may have to pay the difference between what the provider charges and what the plan will pay.

Today, health care providers have formed their own managed care organizations and are competing successfully with the mainstream organizations. Provider owned organizations compete quite well in their local communities but cannot provide needed services to employer groups with employees in multiple states. For companies with employees in multi-state locations, the choice is national and regional PPOs. The problem with many national PPOs is that they are made up of many smaller PPOs which are accessed by the nationals via leased arrangements. This can be effective but presents problems when the providers of the leased networks do not know that their contracts have been leased and refuse legitimate discounts which causes havoc for payors, patients and ultimately employer groups. Thus, there is a need in the art for new and improved methods of selecting health care networks for employer groups with employees in multiple states.

FEATURES OF THE INVENTION

A general feature of the present invention is the provision of improved methods of designing a virtual PPO network for group health care plans which overcome the problems and deficiencies found in the prior art.

A further feature of the present invention is the provision of a new method of designing a virtual PPO network for a group health care plan that seeks to maximize health care savings while minimizing the disruption to plan participants in changing health care providers.

A further feature of the present invention is the provision of a unique method of creating a virtual managed care network spanning more than one state, wherein the virtual network is comprised of a plurality of managed care networks.

A still further feature of the present invention is the provision of a new method of accurately projecting future health care savings by properly designing a virtual PPO network.

These, as well as other features and advantages of the present invention will become apparent from the following specification and claims.

SUMMARY OF THE INVENTION

The present invention includes a new method of creating a client-specific virtual managed care network spanning multiple states. The method seeks to maximize savings while minimizing the inconvenience and disruption to plan participants in changing health care providers. Based upon the utilization or disruption data and projected future savings, one managed care network is selected per state. The various managed care networks selected for each state comprise a virtual health care network for providing health care services to plan sponsors, such as employer groups with employees in multiple states.

The present invention also includes a new method of projecting future health care savings based upon the utilization of a properly designed virtual PPO network. The method generally includes determining historical health care costs for participants for a selected time period, determining a portion of the health care costs that would be in the network, comparing multiple plan discounts to the health care charges incurred or covered in each network, calculating an average expected discount per participant, and then predicting future health care savings based upon the average plan discount per participant and the number of participants projected to be in the network.

The present invention further includes a new method of selecting a group health care plan. The method generally includes determining utilization under the plan based upon the number of probable plan participants that utilize health care providers under the plan, comparing the utilizations for different networks, projecting future savings for networks having the highest utilization, and selecting the networks with the greatest savings.

BRIEF DESCRIPTION OF THE DRAWINGS

The present invention is illustrated by way of example and not limitation in the figures of the accompanying drawings, in which.

DETAILED DESCRIPTION OF A PREFERRED EMBODIMENT

The present invention will be described as it applies to a preferred embodiment. It is not intended that the present invention be limited to the described embodiment. It is intended that the invention cover all modifications and alternatives which may be included within the spirit and broad scope of the invention.

The preferred embodiment is directed to a method of creating a client-specific virtual PPO network which spans multiple states. Those skilled in the art will recognize that the methods disclosed as part of the preferred embodiment can be easily adopted for other types of health care networks and geographic areas.

Figure 1:
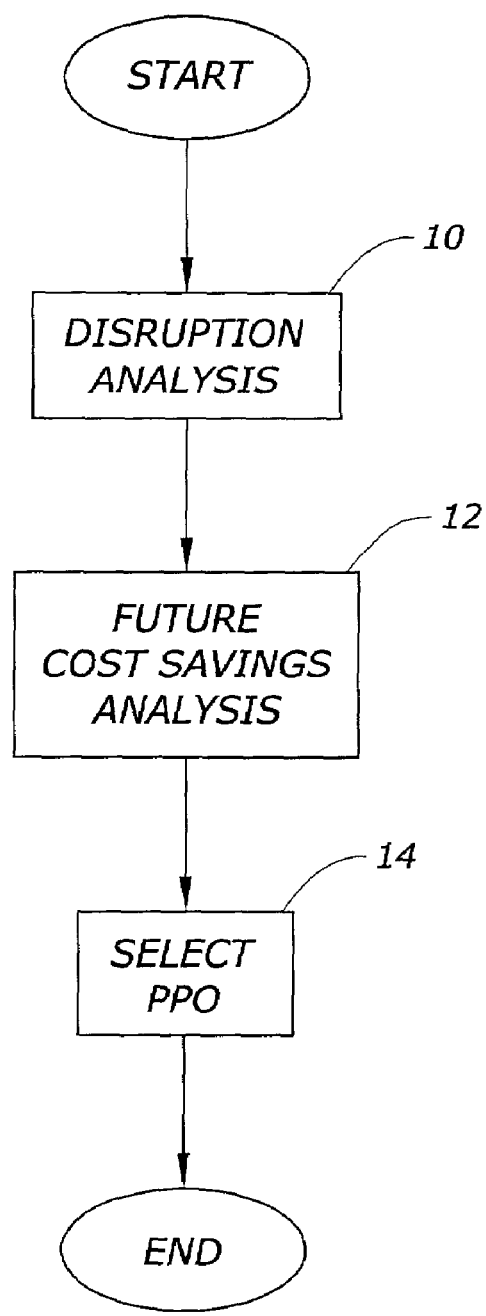
FIGS. 1-3 are flow charts that describe the preferred method of the present invention.

FIG. 1 illustrates the preferred method of creating a virtual PPO network at a high level. Based upon the results of a disruption analysis at step 10 and a determination of future health care cost savings at step 12, a PPO network is selected at step 14.

The purpose of the preferred method of the present invention is to create a client-specific virtual PPO network. There are two primary goals, which are the focus of the preferred method. These goals are to (1) maximize health care savings for the health care plan sponsor while (2) minimizing the disruption and inconvenience to the plan participants (e.g. employees) in changing health care providers. In the past, employer groups had to decide which of these two goals was most important. However, following the methodology of the present invention has shown that these goals are not mutually exclusive.

Before providing further details of the preferred embodiment, it is helpful to have a more complete understanding of the prior art approach in selecting PPOs. Preferably, most PPOs, when soliciting business from a potential plan sponsor, provide a standard GEO Access Report. A GEO Access Report is typically prepared by collecting the residential zip codes of each employee/participant and determining what percentage of participants live within a certain distance of health care providers that are members of the subject PPO. In most cases, the coverage numbers are quite high. For instance, it is not uncommon to have coverage numbers as high as 95% from a GEO Access Report.

The present invention uses a different approach, referred to as a disruption analysis. A disruption analysis shows whether the health care providers presently utilized by the plan participants are in a specific PPO network. Comparing the GEO Access Reports with the disruption data typically shows that coverage is high in the GEO Access Reports, but in reality the utilization based on the disruption data is approximately half of what it depicted in the GEO Access Reports. Most national networks will have coverage based upon GEO Access data that ranges from 80-95% for multi-state health care plans. Yet when evaluating using the method of present invention, actual utilization is usually 35-45%. This translates into half the expected savings from a given network. For the GEO Access Reports to be accurate, there must be significant financial disincentives to force the plan participants to use health care providers in the network. One of the goals of the present invention in building a virtual PPO network is to maximize the largest number of member health care providers already utilized by participants. In this respect, disruption data is a much more valuable tool in the selection process.

Figure 2:
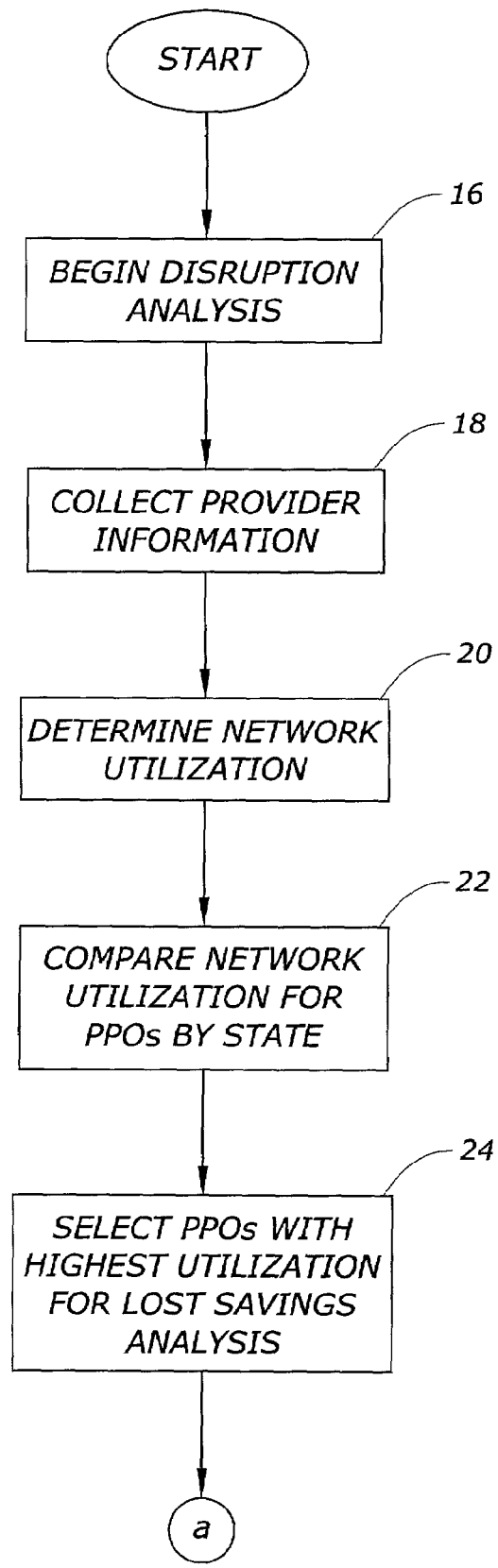
Figure 3:
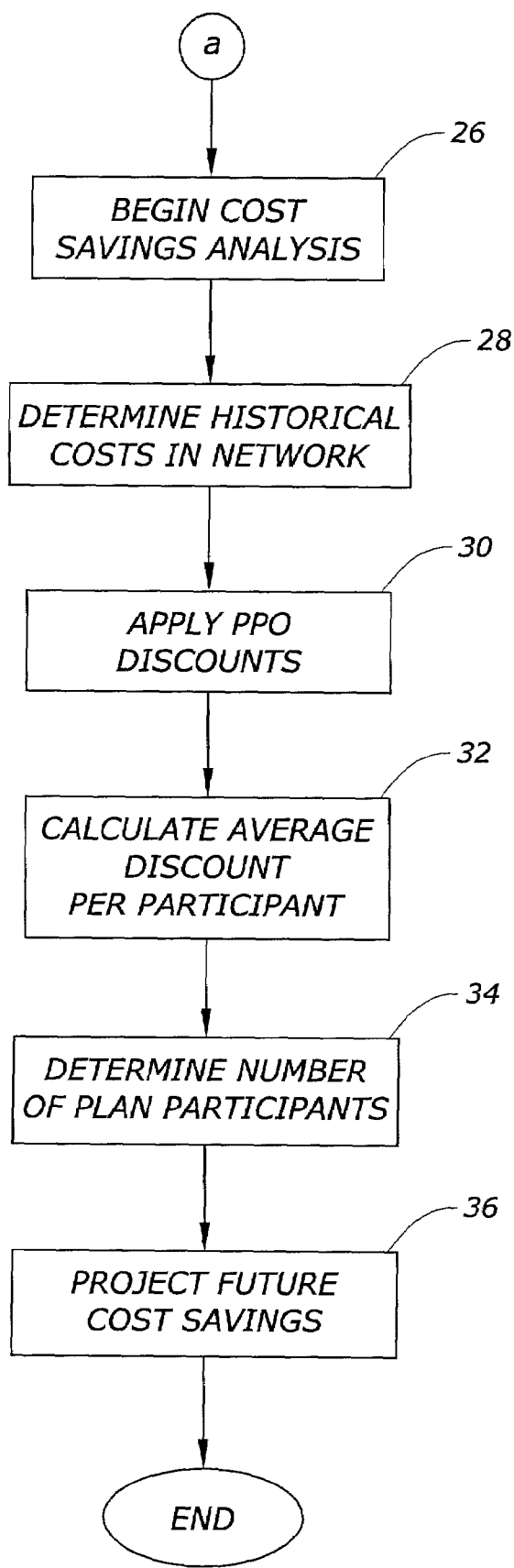

FIGS. 2 and 3 illustrate in greater detail the preferred method of creating a virtual PPO. The method begins step 16 with a disruption analysis. Health care provider information is collected at step 18 to help determine utilization for a particular PPO. One way to obtain this information is to request a database-delimited file or spreadsheet containing a list of medical providers who have been paid for medical services by the plan sponsor in the past year. Such data preferably includes the following items: (1) the Federal Tax Identification Number (TIN) of each health care provider to which payments were made; (2) the name of the health care provider as listed in the plan sponsor's claims system; (3) the location of the health care provider by city and state; and (4) dollars paid to each health care provider. It is preferred that health care providers paid only a minimal amount during the preceding year (e.g. less than $300) be removed from the list because the percentage of health care providers paid such amounts as typically minimal. The present invention seeks to provide an evaluation based upon where the majority of the plan sponsor's claims dollars are spent.

In order to determine provider utilization, the various national and regional PPO networks are presented with the list of the data referenced above and asked to identify the health care provider and tax ID numbers that are members of their specific health care network.

At step 20, network utilization is determined. The data compiled at step 18 is preferably compared on the following basis: For each PPO, the number of health care provider matches on a state-by-basis is used to calculate the percentage of providers that would be classified as "in-network." The total number of dollars spent in each network and the percentage of dollars spent in each network are also computed. With these measures of network utilization, PPOs can be compared on a state-by-state basis at step 22.

As previously noted, the goal is to maximize the utilization factor to minimize the disruption to participants in changing health care providers. Those PPOs with the highest utilization are thus selected for a cost savings analysis at step 24. It is preferred that multiple (5 or more) PPOs be evaluated for each state. However, the selection of PPOs for the cost savings analysis must be made on a case-by-case basis, sometimes requiring more than one PPO per state.

FIG. 3 illustrates the steps performed in the cost savings analysis. The cost savings analysis begins at step 26. The starting point is to determine historical health care costs that are "in-network" for a particular time period, preferably one year (see step 28). One way to obtain the cost data is from a report of approved charges from the claims payor. These are the charges that are approved for payment, which tends to be the most accurate starting point. An alternative approach is to review an IRS 1099 report that is provided to the IRS for tax purposes. Such a report lists all of the vendors the plan sponsor paid in excess of $600 in the year prior that were reported to the IRS. While these reports contain information on all vendors, it is fairly easy to separate the health care vendors. Estimating health care costs based upon the 1099 report tends to be less accurate, however. The reason is that the 1099 report is based on what was actually paid. The total charges have been reduced by deductibles, co-pay amounts, reductions resulting from usual and customary adjustments, existing PPO arrangements, and passive discounting of medical claims. As a result, dollar amounts from the 1099 report must be grossed up to present an accurate starting point. It has been found that in the case of the average plan, the 1099 amounts must be grossed up by 40% or more.

Once the historical heath care costs are computed, the appropriate PPO discounts are applied at step 30. The discounts are provided by the PPOs. The PPO knows when contracting with a health care provider what the discounts will be. The discounts are typically either a percentage off of bill charges, a percentage of resource based relative value scale (RBRVS) or a daily rate (per diem).

It is preferable to separate the total health care charges between hospital charges, on the one hand, and physician and other charges, on the other. The hospital charges are multiplied by the average discount for hospital charges in the specific state of the applicable PPO. The process is repeated for the physician and other charges. The predicted savings for both hospital and physician and other charges are combined and divided by the total charges determined to be in the PPO. The resulting percentage is used as the average discount for each network in each particular state. The average discount is then calculated on a per participant basis at step 32.

A determination is made to as to the number of participants projected to be the in plan for the future at step 34. The future savings can then be computed at step 36. Those skilled in the art will appreciate that there are various other ways to project future savings based upon PPO discounts. The method described herein is exemplary only.

Those skilled in the art will appreciate that the methods described as part of the methods described as part of the preferred embodiment can be implemented and automated with computer systems. In particular, the acquisition and manipulation of the data can be easily computerized. Further, data calculations can be performed more efficiently by computers. Computers and computer systems are also well-suited to create and generate reports.

In the preceding detailed description, the invention is described with reference to a specific exemplary embodiment thereof. Various modifications and changes may be made hereto with departing from the broader scope and spirit of the invention as set forth in the claims. The specification and drawings are, accordingly, to be regarded in an illustrative rather than a restrictive sense. The invention is to be limited only by the claims appended hereto.

What is claimed is:

1. A computer-assisted method implemented using a computer of creating a virtual health care network that spans multiple states and seeks to maximize health care savings while minimizing an inconvenience to participants in changing health care providers, the method comprising:

identifying a plurality of health care networks in each of the states for analysis wherein each of the health care networks comprises a plurality of health care providers and has been utilized by one or more of the participants;

for each of the plurality of health care networks, collecting information concerning utilization of the health care providers in the network by the participants;

computing measures of network utilization for each of the plurality of health care networks using a computer, wherein the measures of network utilization comprise number of the participants who utilize the health care providers in the network, a percentage of the participants who utilize the health care providers in the network, a measure of total health care costs in the network, and a measure of a percentage of health care costs in the network;

comparing the measures of network utilization in each of the states for the health care networks;

selecting one or more health care networks for each state based on the measures of network utilization to provide a reduced number of health care networks for each state;

for each of the one or more health care networks selected as part of the reduced number of health care networks for each state, projecting future health care savings accruing over the network;

wherein the future health care savings are projected based upon historical hospital charges and historical physician charges for the participant, health care network discounts for hospital charges, health care network discounts for physician charges, and a portion of the historical health care costs projected to fall to a health care provider in the network;

selecting one or more of the health care networks per state having a highest projected savings from the reduced number of health care networks for each state to thereby further reduce number of health care networks associated with each state;

forming a virtual health care network from the one or more health care networks per state having the highest projected savings to thereby maximize health care savings while minimizing inconvenience to participants in changing health care providers for participants in the virtual health care network; and providing an output from the computer indicative of the virtual health care network.

2. The method of claim 1 wherein the health care network is a managed care network.

3. The method of claim 2 wherein the managed care network is a preferred provider organization (PPO).

4. A computer-assisted method implementing using a computer of creating a virtual network from a plurality of networks that seeks to maximize savings under a health care plan, each of the networks comprising a plurality of health care providers, the method comprising:

for each of the group health care networks, collecting information concerning a number representing potential plan participants who utilize one of the health care providers of the networks;

determining network utilization for each of the networks in the plurality of networks based upon the number of potential plan participants who utilize one of the health care providers in the networks, a percentage of the participants who utilize the health care providers in the network, a measure of total health care costs in the network, and a measure of a percentage of the health care costs in the network;

comparing the utilizations for the networks;

identifying a reduced set of the networks with a highest utilization, the reduced set of the networks less than a total number of networks;

for each of the networks in the reduced set of networks, calculating future savings for the network based upon historical hospital charges and physician charges for plan participants, network discounts for hospital charges and network discounts for physician charges, and a portion of the historical health care costs projected to fall to one of the health care providers in the network, wherein the step of calculating is performed using a computer;

selecting one or more of the networks having greatest future savings;

forming a virtual network from the one or more of the networks having greatest future savings to maximize savings under the health care plan;

providing an output from the computer indicative of the virtual health network.

5. The method of claim 4 wherein the network is a preferred provider organization (PPO).

6. The method of claim 5 wherein the PPO is selected for a particular state.

* * * * *